United States Patent
Wepplo et al.

(10) Patent No.: US 6,441,190 B1
(45) Date of Patent: Aug. 27, 2002

(54) PROCESS OF THE PREPARATION OF CHIRAL NICOTINIC, QUINOLINIC OR BENZOIC ACID IMIDAZOLINONE HERBICIDES

(75) Inventors: Peter John Wepplo, Princeton; Thomas Walter Drabb, Trenton, both of NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/046,339

(22) Filed: Jan. 14, 2002

Related U.S. Application Data

(63) Continuation of application No. 09/563,350, filed on May 3, 2000, now Pat. No. 6,339,158.
(60) Provisional application No. 60/132,188, filed on May 3, 1999.

(51) Int. Cl.⁷ .............................................. C07D 233/40
(52) U.S. Cl. .................................................... 548/318.5
(58) Field of Search ...................................... 548/318.5

(56) References Cited

U.S. PATENT DOCUMENTS 4,554,013 A * 11/1985 Los ................................ 71/92

* cited by examiner

Primary Examiner—T. A. Solola
Assistant Examiner—Joseph Murray
(74) Attorney, Agent, or Firm—Keil & Weinkauf

(57) ABSTRACT

There is provided a stereospecific process for the preparation of essentially enantiomerically pure imidazolinone herbicides having the R-configuration via (R) 2-amino-2,3-dimethylbutyronitrile.

9 Claims, No Drawings

PROCESS OF THE PREPARATION OF CHIRAL NICOTINIC, QUINOLINIC OR BENZOIC ACID IMIDAZOLINONE HERBICIDES

This is a divisional of application Ser. No. 09/563,350 filed May 3, 2000, now U.S. Pat. No. 6,339,158 the entire disclosure of which is hereby incorporated by reference. which claims benefit of Prov. No. 60(132,188 filed May 3, 1999.

BACKGROUND OF THE INVENTION

Imidazolinone compounds, for instance, those described in U.S. Pat. Nos. 4,188,487; 4,798,619 and 5,334,576, are highly potent, broad spectrum, environmentally benign, herbicidal agents. In general, the herbicidal activity of the R-isomer is better than that of the racemic imidazolinone compound. A process to prepare chiral imidazolinones via the resolved optically active 2-amino-2,3-dimethylbutyramide enantiomers is described in U.S. Pat. No. 4,683,324. Said aminoamide enantiomers are prepared via the hydrolysis of their chiral 2-amino-2,4-dimethylbutyronitrile precursors and are difficult to isolate.

Therefore, it is an object of this invention to provide a stereospecific process to prepare chiral nicotinic, quinolinic or benzoic acid imidazolinone herbicidal agents directly from (R)2-amino-2,3-dimethylbutyronitrile without loss of optical purity and without the prior formation of (R)2-amino-2,3-dimethylbutyramide.

SUMMARY OF THE INVENTION

The present invention provides a stereospecific process to prepare a chiral compound of formula I

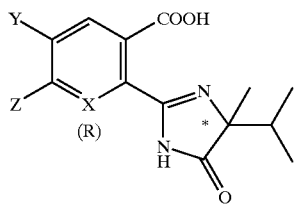

(I)

wherein
  X is N or CH; and
  Y and Z are each independently H, $C_1$–$C_4$alkyl optionally substituted with one $C_1$–$C_4$alkoxy group or Y and Z may be taken together to form a group —CH=CH—CH=CH—
which process comprises the following steps:
  a) reacting a compound of formula II

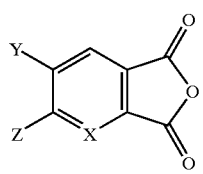

(II)

wherein X, Y and Z are as described hereinabove with at least one molar equivalent of (R)2-amino-2,3-dimethylbutyronitrile in the presence of a non-polar, essentially water-free solvent, optionally in the presence of a tertiary amine, to form a first reaction mixture;

b) hydrolyzing said reaction mixture in aqueous acid to form an acidic second reaction mixture;
  c) reacting said second reaction mixture with an excess of an aqueous base at a temperature of about 20°–85° to form a basic third reaction mixture;
  d) separating said third reaction mixture to obtain an aqueous phase; and
  e) acidifying said aqueous phase to obtain the desired chiral formula I imidazolinone compound.

DETAILED DESCRIPTION OF THE INVENTION

Chiral imidazolinone compounds having the R configuration demonstrate about a 2-fold increase in herbicidal activity over the corresponding racemic mixture. Heretofore, (R)imidazolinone compounds were prepared from (R)2-amino-2,3-dimethylbutyramide due to the instability of the (R)2-amino-2,3-dimethylbutyronitrile compound. However, isolation of said (R)aminoamide is difficult. Surprisingly, it has now been found that chiral imidazolinone herbicides may be prepared directly from (R)2-amino-2,3-dimethylbutyronitrile in the presence of a non-polar essentially water-free solvent with substantially complete retention of enantiomeric purity from the (R)aminonitrile starting material to the final chiral imidazolinone herbicidal product. Advantageously, the process of the invention eliminates the need for the prior formation of (R)2amino-2,3-dimethylbutyramide.

In accordance with the process of the invention, a formula II anhydride is reacted with at least one molar equivalent of (R)2-amino-2,3-dimethylbutyronitrile in the presence of a non-polar, essentially water-free solvent, optionally in the presence of a tertiary amine, to form a first reaction mixture; said reaction mixture is hydrolyzed with aqueous acid to form an acidic second reaction mixture; said second reaction mixture is treated with an excess of a base at a temperature of about 20°–90° C. to form a basic third reaction mixture; said third reaction mixture is separated to obtain an aqueous phase; and the aqueous phase is acidified to obtain the desired chiral formula I imidazolinone herbicide. The process is illustrated in flow diagram I. In the specification and claims, an asterisk designates the assymetric carbon upon which the (R) configuration is conferred.

Flow Diagram I

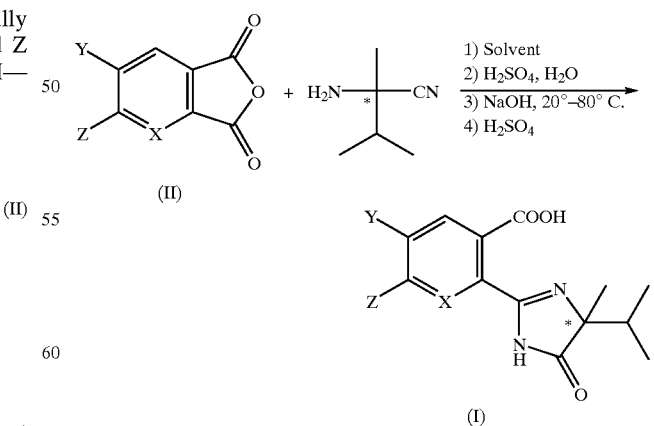

Solvents suitable for use in the process of the invention are non-polar essentially water-free solvents such as aromatic hydrocarbons (e.g. toluene, benzene, xylene, naphthalene and the like, preferably toluene), halogenated aromatic hdrocarbons (e.g. chlorobenzene, dichlorobenzenes and the like), hydrocarbons (e.g. pentanes, hexanes and the like), halogenated hydrocarbons (e.g. chloroform, methylene chloride, dichlorethane, and the like, esters (e.g. ethyl acetate, methyl propionate and the like), ethers (e.g. diethyl ether, tetrahydrofuran, dioxane and the like) or any of the conventional, preferably water immiscible, organic non-polar solvents.

Preferred non-polar solvents suitable for the process of the invention are aromatic hydrocarbons, particularly toluene.

Tertiary amines suitable for use in the first step of the inventive process are pyridine, 4-cyanopyridine, 4-picoline, 2-picoline, mixed picolines, tri($C_1$–$C_4$)alkylamine, quinoline or any of the conventional organic tertiary amines, preferably 4-picoline. The amine may be present in amounts ranging from catalytic to excess amounts such as 10 mole % to 4.0 molar excess.

Acids suitable for use in the process of the invention include strong mineral acids such as HCl or $H_2SO_4$, preferably $H_2SO_4$.

Bases suitable for use in the inventive process include alkali metal hydroxides or alkoxides, preferably hydroxides such as NaOH or KOH, preferably NaOH. These may be present at about 2 to 20 molar-equivalents, preferably about 2 to 8 molar-equivalents.

It is also intended that the process of the invention embraces the use of (S)-2,3-dimethylbutyronitrile to prepare the corresponding (S)-imidazolinone herbicidal product.

In actual practice, a mixture of the formula II anhydride in a non-polar, essentially water-free solvent, preferably an aromatic hydrocarbon, more preferably toluene, is treated with a 10% to 60% solution of (R)2-amino-2,3-dimethylbutyronitrile in a non-polar, essentially water-free solvent, preferably an aromatic hydrocarbon, more preferably toluene, optionally in the presence of 10 mol % to 4.0 molar excess, preferably about 10 mol % to 1.0 molar equivalent of 4-picoline, at a temperature of about 5° to 45° C., preferably about 5° C. to 30° C., to form a first reaction mixture; said mixture is treated with a strong mineral acid, preferably $H_2SO_4$, and water at temperatures of about 5° to 80° C., preferably about 20° C. to 60° C. to form an acidic second reaction mixture; said second mixture is treated with an excess, (about 2 to 20 moles per mole of acid used in the previous hydrolysis step) of an aqueous alkali metal hydroxide or alkoxide, preferably an alkali metal hydroxide, more preferably NaOH or KOH, of 10% or greater concentration on a weight basis at temperatures of about 15° C. to 90° C., preferably 20° C. to 85° C., to form a basic third reaction mixture; said third reaction mixture is separated to obtain an aqueous phase; and said aqueous phase is acidified with a strong mineral acid such as HCl, HBr or $H_2SO_4$, preferably $H_2SO_4$, to a pH of about 2 to 4 to obtain the desired chiral formula I imidazolinone product. The product may be isolated using conventional procedures such as filtration, extraction with a suitable solvent, chromatographic separation and the like, preferably filtration or extraction.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight. NMR designates nuclear magnetic resonance. HPLC designates high performance liquid chromatography.

EXAMPLE 1

Preparation of (R)2-(4-isopropyl-4-methyl-5-oxo-2-imidazolin-2-yl-5-methylnicotinic acid

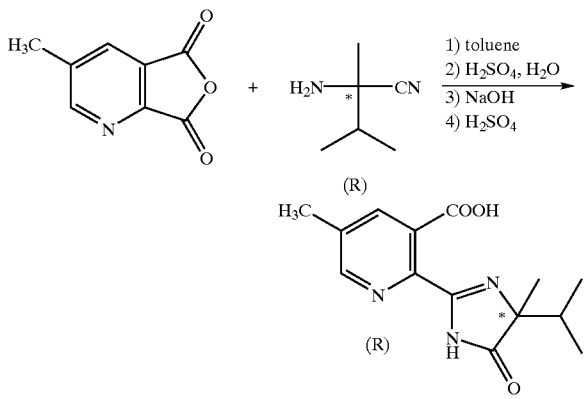

A dry solution of (R)2-amino-2,3-butyronitrile (18.2 g, 0.163 mol) in 120 ml of toluene is added to a mixture of 5-methylpyridine-2,3-dicarboxylic acid anhydride (16.3 g, 0.10 mol) in toluene and 4-picoline (0.01 mol) over a 1 hour period at 10° C. The reaction mixture is stirred 10° C. for 2 hr, treated with concentrated $H_2SO_4$ (6.33 ml, 11.65 g, 0.14 mol) and water under nitrogen at 30°–50° C., stirred for 5 hr at 50° C., treated with NaOH (51.4 g, 1.28 mol) as a 50% aqueous solution at 20° C. to 80° C. and treated with water. The reaction mixture is cooled to room temperature and the phases are separated. The aqueous phase is acidified to pH 3 with concentrated $H_2SO_4$, cooled and filtered. The filtercake is dried in vacuo at 60° C. for 72 hr to give the title product as a white solid, 16.2 g (58.7% yield) $[\alpha]_D^{25}$=+10.98°, 92.15%(R). Quantitative NMR analysis indicates 99.8% purity, 95%(R) isomer.

EXAMPLE 2

Preparation of (R)2-(4-isopropyl-4-methyl-5-oxo-2-imidazolin-2-yl-5-nicotinic acid

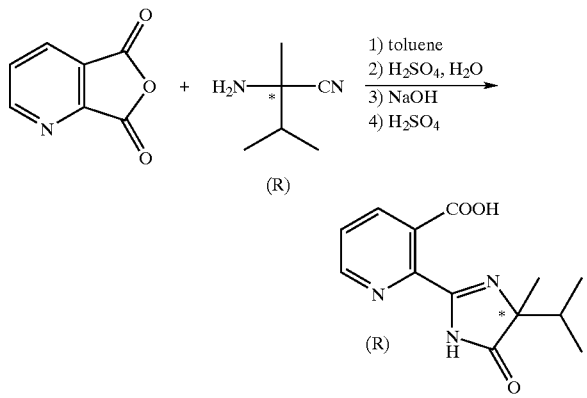

A dry solution of (R)2-amino-2,3-dimethylbutyronitrile (168 g, 1.5 mol) in 750 ml of toluene is added to a mixture of pyridine-2,3-dicarboxylic acid anhydride (149.1 g, 1.0 mol) in toluene and 4-picoline (0.01 mol) over a 1 hr period at 10° C. The reaction mixture is stirred at 5°–10° C. for 1 hr., then stirred at 20° C. for 1 hr., treated with 200 ml $H_2O$, then treated quickly with 102 g of concentrated $H_2SO_4$ over a 3–5 minute period at 20°–40° C., heated to 60° C., held at 60° C. for 2.5 –3 hr. cooled to 20°, treated with 50% NaOH (412.5 ml, 631.2 g, 7.89 mol) at 20° C. to 80° C., treated with 240 ml H$_2$O and cooled to room temperature. The phases are separated. The aqueous phase is acidified to pH 3 with concentrated H$_2$SO$_4$, extracted with methylene chloride, diluted with 1 L H$_2$O and extracted twice more with methylene chloride. The organic extracts are combined, dried over MgSO$_4$ and concentrated in vacuo to a thick slurry. The slurry is diluted with hexanes, stirred for 45 minutes and filtered. The filtercake is dried in vacuo at 50°–55° C. to give the title product as a white solid, 219.4 g (84% yield), mp 128–131° C. (bubbling). Quantitative NMR analysis indicates 95.4% purity, 95% R isomer.

EXAMPLE 3

Preparation of (R)2-(4-isopropyl-4-methyl-5-oxo-2-imidazolin-2-yl)-3-quinolinecarboxylic acid

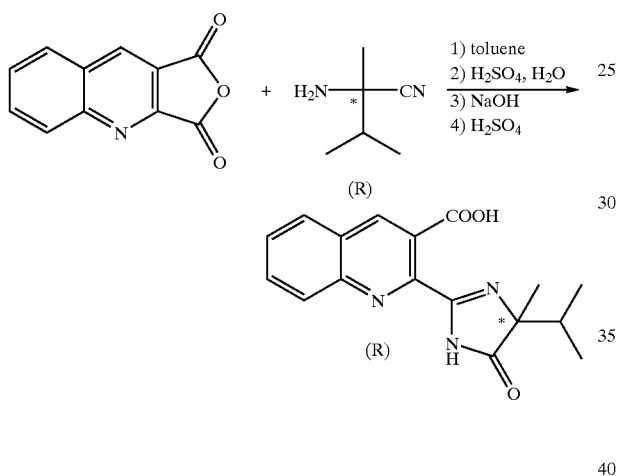

A dry solution of (R)2-amino-2,3-dimethylbutyronitrile (11.8 g, 0.105 mol, 91% R isomer) in toluene (37% w/w concentration) is added to a stirred slurry of quinoline-2,3-dicarboxylic acid anhydride (19.9 g, 0.10 mol) in a mixture of toluene and picoline (0.01 mol) at room temperature over a 45 minute period and stirred at room temperature for 1 hour. The reaction mixture is then treated in essentially the same manner as described in Example 1 to obtain the title product as a tan solid, 29.4 g (78% yield), 91.8% R isomer by chiral HPLC analysis.

EXAMPLE 4

Preparation of (R)5-Ethyl-2-(4-isopropyl-4-methyl-5-oxo-2-imidazolin-2-yl)nicotinic acid

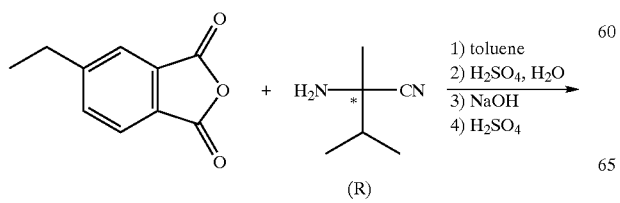

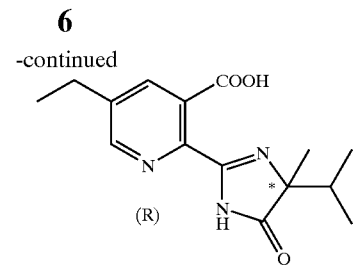

A dry solution of (R)2-amino-2,3-dimethylbutyronitrile (12.3 g, 0.109 mol, 93.1% R isomer) in toluene (32% w/w concentration) is added to a stirred slurry of 5-ethylpyridine-2,3-dicarboxylic acid anhydride (17.7 g, 0.10 mol) in a mixture of toluene and picoline (0.01 mol) at room temperature over a 40 minute period and stirred at room temperature for 1 hour. The reaction mixture is then treated in essentially the same manner as described in Example 1 to obtain the title product as an off-white solid, 21.2 g (72% yield), 92.5% R isomer by chiral HPLC analysis.

EXAMPLE 5

Preparation of (R)2-(4-isopropyl-4-methyl-5-oxo-2-imidazolin-2-yl)-5-(methoxymethyl)nicotinic acid

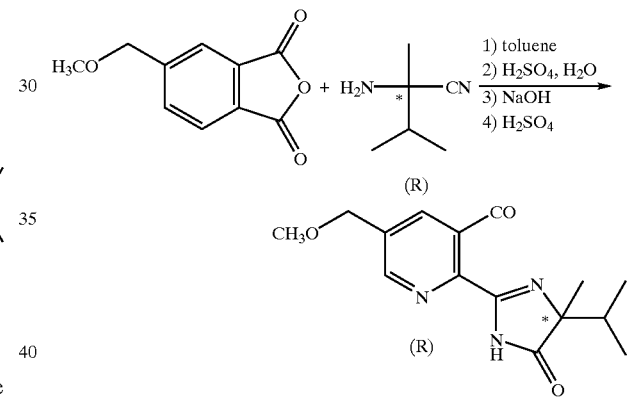

A dry solution of (R)2-amino-2,3-dimethylbutyronitrile (12.3 g, 0.109 mol, 92.9% R isomer) in toluene (38% w/w concentration) is added to a stirred mixture of 5-(methoxymethyl)pyridine-2,3-dicarboxylic acid anhydride (19.3 g, 0.10 mol) in a mixture of toluene and picoline (0.01 mol). The reaction mixture is then treated in essentially the same manner as described in Example 1 to obtain the title product as a tan solid, 28.8 g (79% yield), 92.5% R isomer by chiral HPLC analysis.

What is claimed is:
1. A process for the preparation of a chiral compound of formula I

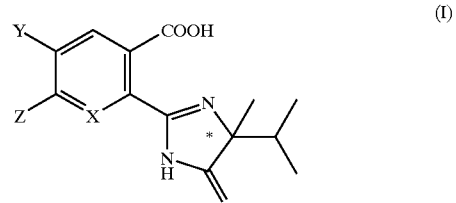

wherein
- X is CH; and
- Y and Z are each independently H, $C_1$–$C_4$alkyl optionally substituted with one $C_1$–$C_4$alkoxy group or Y and Z may be taken together to form a group —CH=CH—CH=CH— which process comprises the following steps:

a) reacting a compound of formula II

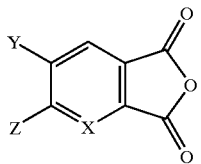
(II)

wherein X, Y and Z are as described hereinabove with at least one molar equivalent of chiral 2-amino-2,3-dimethylbutyronitrile

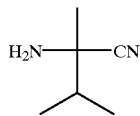

in the presence of a non-polar, essentially water-free solvent, optionally in the presence of a tertiary amine, to form a first reaction mixture;

b) hydrolyzing said reaction mixture in aqueous acid to form an acidic second reaction mixture;

c) reacting said second reaction mixture with an excess of an aqueous base at a temperature of about 15° C. to 90° C. to form a basic third reaction mixture;

d) separating said third reaction mixture to obtain an aqueous phase; and e) acidifying said aqueous phase to obtain the desired chiral formula I imidazolinone compound.

2. The process according claim 1 wherein the non-polar essentially water-free solvent is selected from the group consisting of aromatic hydrocarbons, halogenated aromatic hydrocarbons, hydrocarbons, halogenated hydrocarbons, esters and ethers.

3. The process according to claim 2 wherein the solvent is an aromatic hydrocarbon.

4. The process according to claim 3 wherein the non-polar, essentially water-free solvent is toluene.

5. The process according to claim 1 wherein the acid in steps b and e is HCl or $H_2SO_4$.

6. The process according to claim 5 wherein the acid is $H_2SO_4$.

7. The process according to claim 1 wherein the base in step c is an alkali metal hydroxide and the temperature is about 15° C. to 90° C.

8. The process according to claim 7 wherein the base is NaOH.

9. The process according to claim 1 wherein the chiral 2-amino-2,3-dimethylbutyronitrile is (R) 2-amino-2,3-dimethylbutyronitrile.

* * * * *